(12) United States Patent
Baehler et al.

(10) Patent No.: US 6,383,223 B1
(45) Date of Patent: May 7, 2002

(54) ENDOPROSTHESIS FOR A JOINT, ESPECIALLY A FINGER, TOE OR WRIST JOINT

(76) Inventors: André Baehler, Kapfsteig 44, CH-8032 Zürich; Beat R. Simmen, Tennenberg, CH-8317 Tagelswangen, both of (CH)

(*) Notice: Subject to any disclaimer, the term of this patent is extended or adjusted under 35 U.S.C. 154(b) by 0 days.

(21) Appl. No.: 09/445,456
(22) PCT Filed: Jun. 17, 1998
(86) PCT No.: PCT/CH98/00262
 § 371 Date: Dec. 17, 1999
 § 102(e) Date: Dec. 17, 1999
(87) PCT Pub. No.: WO98/57600
 PCT Pub. Date: Dec. 23, 1998

(30) Foreign Application Priority Data

Jun. 18, 1997 (CH) .............................................. 1485/97

(51) Int. Cl.⁷ .................................................. A61F 2/42
(52) U.S. Cl. ................................ 623/21.11; 623/21.12; 623/21.15; 623/21.19; 623/16.11
(58) Field of Search ............................ 623/21.15, 21.19, 623/21.11, 20.32, 20.27, 21.16, 21.17

(56) References Cited

U.S. PATENT DOCUMENTS

| 3,593,342 A | 7/1971 | Niebauer et al. ............. 3/1 |
| 3,875,594 A | 4/1975 | Swanson ....................... 3/1 |
| 5,534,033 A | * 7/1996 | Simpson ..................... 623/18 |
| 5,549,681 A | 8/1996 | Segmüller et al. ............ 623/18 |

FOREIGN PATENT DOCUMENTS

| DE | 1960087 | 7/1970 |
| DE | 3630138 A1 | 3/1988 |
| EP | 057597 A2 | 8/1982 |
| EP | 577179 A1 | 1/1994 |
| EP | 600557 A2 | 7/1994 |
| EP | 684024 A2 | 11/1995 |
| FR | 2242067 | 3/1975 |
| FR | 2736536 | 1/1997 |
| WO | WO 91/04718 | 5/1991 |
| WO | WO 91/07149 | 5/1991 |
| WO | WO 92/22266 | 12/1992 |
| WO | WO 96/25129 | 8/1996 |
| WO | WO 96/41596 | 12/1996 |

* cited by examiner

Primary Examiner—David J. Isabella
Assistant Examiner—Urmi Chattopadhyay

(57) ABSTRACT

In an endoprosthesis (11*h*) for a joint, the two interacting joint parts (15*h*, 16*h*) are joined by a cord-type connection piece (21*h*), which is attached in the vicinity of the body axis (M2*h*, M2*h*′) of the convex condyle (15*h*) and extends through a longitudinal groove (22*h*) in the flexion direction of the joint. The connection piece assures a play space (31*h*) between the contact surfaces (19*h*, *h*′, 20*h*, *h*′) of joint (11*h*). It is protected from friction on groove wall (55*h*, 55*h*′) by an elevation (50*h*, 43*h*) in concave joint part (16*h*). An elevation (43*h*, 50*h*) at concave joint part (16*h*) and a depression (49*h*) at convex joint part (15*h*) interact in such a way that the lateral movement play space between depression and elevation determines the freedom of movement with respect to the lateroflexion of the joint. In preferred forms of embodiment, thanks to the spherical surfaces at least one pair of corresponding sliding surfaces (19*h*, 20*h*; 20*h*′) on the two condyles lie flatly on one another, under load, in any position of the joint.

18 Claims, 7 Drawing Sheets

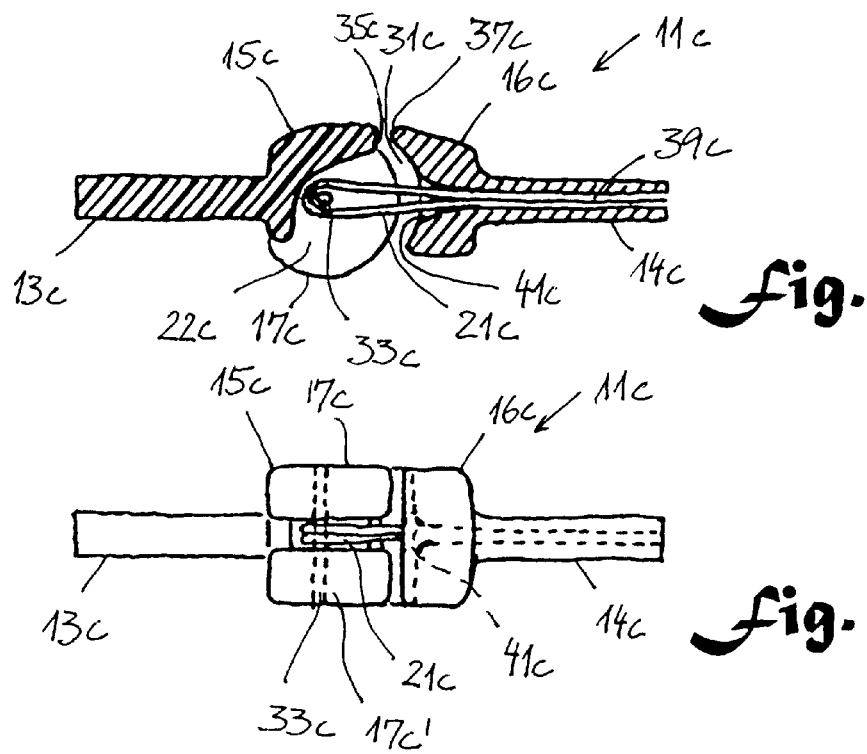
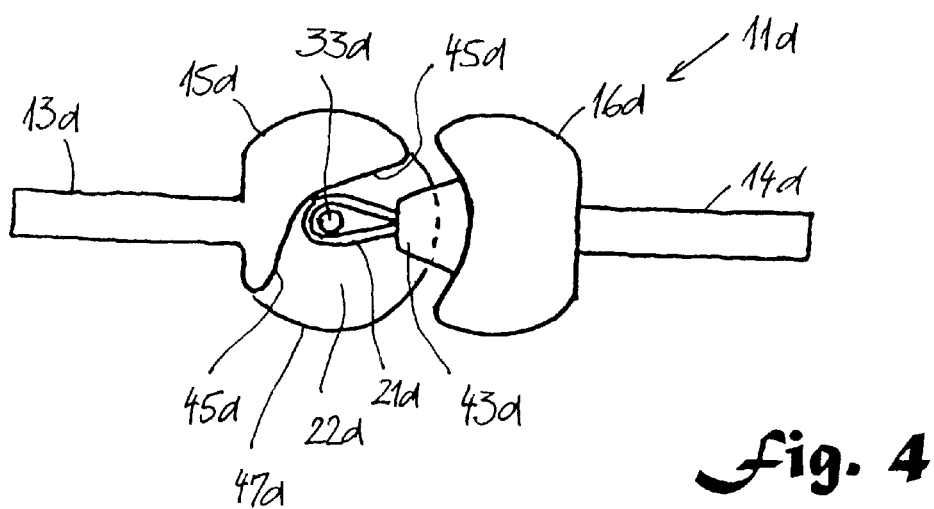

ly an elastic element in the connection piece. On the other

ENDOPROSTHESIS FOR A JOINT, ESPECIALLY A FINGER, TOE OR WRIST JOINT

TECHNICAL FIELD OF THE INVENTION

The present invention concerns an endoprosthesis for a joint, particularly a finger, toe or hand joint, with a proximal and a distal joint part, of which one joint part in the flexion direction has an essentially convex contact surface around a body axis and the other has a correspondingly essentially concave contact surface, and which joint parts are joined by means of a flexible connection piece that takes up tensile forces, which piece has a thread-type or tape-type element.

PRIOR ART

The natural metacarpophalangeal joint (MCP) gives the finger a lateral freedom of movement, which differs each time depending on the flexion of the joint. In flexion, the degree of freedom is laterally zero to only a few degrees, but in extension it is approximately 30 degrees. In addition, a limited passive rotation is possible around the axis of the finger. The interphalangeal joint leaves free almost no movement play space laterally, independent of the flexion angle, and the joint parts can rotate only very slightly relative to one another. Therefore, each joint has its own particular degree of freedom with respect to extension and flexion, relative to rotation, but also relative to lateroflexion.

In order to permit natural movements of flexion, extension, and rotation around the joint, while, however, controlling the movement path of the finger opposite the metacarpus, in French patent application FR-A1-2,736,536, an endoprosthesis is proposed for a finger joint, which has a proximal joint part, a corresponding concave distal joint part and a connection and "programmable" part with a rod made of a pliant material. The rod sits in both joint parts in a guide channel, which is arranged axially in the pin of the joint part to be inserted in the bone marrow channel and begins with approximately cylindrical shape and spreads out into trumpet shape with decreasing distance to the condyle surface. The movement play space is defined by the interaction of guide channel and connection rod. Shape, dimensions and possibly the pre-programming of an alloy with "shape memory" of the connection rod determine the course of movement of the joint.

Such a joint has the disadvantage that the pliant connection rod must fulfill a multiple number of tasks simultaneously. Thus it must be pliable differently in different directions, but it must be resistant to abrasion, and in any case, it must have a shape memory. It must have a certain stiffness, yet it must be flexible. In addition, the material should be compatible with the body and long-lasting, i.e., it should not be fatigued.

An orthopedic prosthesis implant is proposed in U.S. Pat. No. 5,534,033, in which the joint parts each have a cup that can be inserted into the bone marrow channel, and in the hollow cavity of this cup is attached a condyle of ceramics or carbon by means of an elastomeric adhesive, whereby the condyles contact one another in a sliding manner and both joint parts are joined by connection means. The connection means comprise either an envelope enclosing the condyles or a thread, which is guided through a hole in the condyles. Also, two threads at a distance relative to one another are proposed. These threads can be guided through holes in the condyles or also guided around the condyle. The function of the threads consists of guiding the joint parts in such a way that they are not dislocated. It cannot be derived from the document how the connection means react to a movement of the joint. It is assumed that the connection means must be either elastic (knitted DACRON fiber (trademark of E.I. duPont de Nemours and Company, Wilmington, Del.)) or are fastened to a spring. In any case, it can be derived from the drawings and the description that the distance between the attachment points of the connection means changes in length upon movement of the joint. However, this solution brings its own disadvantages. The threads, which are guided through the holes, can be sheared off by the edges of the holes at the condyle surface, or they can end up between the condyles and can be abraded therein. If the threads are guided around the condyles, they rub against the condyles and do not assure sufficient safety from dislocation when the joint is bent. The envelopes are stretched at any flexion on the upper side of the joint, or in the case of the extended joint, folded material of the envelope is present on the upper side.

OBJECT OF THE INVENTION

It is thus the object of the invention to create an endoprosthesis for small joints, in which the mentioned disadvantages will be avoided, and a flexible connection of both joint parts that guarantees a play space will be assured. The connection will be loose enough and offers such little resistance, that the two parts can move freely, like the natural joint. The connection piece will not become fatigued. The movement play space of the joint will be definable with respect to rotation, extension, flexion and lateroflexion, and the latter will be dependent on extension, with a simultaneous loose holding together of the joint parts. An abrasion that is as small as possible will be assured.

DESCRIPTION OF THE INVENTION

According to the invention, this is achieved by the fact that the connection piece assures a defined play space between the contact surfaces, that a groove longitudinally extended in the flexion direction is formed in the convex joint part, that the connection piece is attached in this groove or at the base of this groove, whereby a lateral play space exists between groove and connection piece. In this way, there is a large freedom of movement in the flexion direction and simultaneously there is a definable, usually smaller freedom for a displacement or lateral deflection as well as a rotation. However, the joint is guided and protected against dislocation, since the connection of the two joint parts with a connection piece prevents a luxation.

When fibers of threads and fabrics or of flat tapes and thin membranes are flexed, the material is very slightly stretched and compressed in the direction of the flexion movement, due to the small dimension of the cross section. Fibers, tapes and membranes are consequently more suitable for flexible, pliant connection, the thinner the material cross-section. This property of fibers and tapes also holds true when they are spun and/or woven into large dressings or bandages, in order to be able to take up multiple tensile loads. Such bandages may be formed by spinning, weaving or knotting and have the shape of cords and ropes, tubings, tapes strips or flat woven fabrics. Essentially, the very small dimensions of the material in at least one dimension are suitable for flexion in one direction, and in two dimensions for flexion in several directions. The load capacity of such thread-type, tape-type or membrane-type parts makes them very useful for tensile designs. In addition, their resistance to fatigued fractures is assessed. High resistance to tearing with simultaneous resistance to fracture is realized and utilized, for example, in cords, ropes, nets, belts, tubings, membranes and foils of all types.

For endoprostheses for small joints, the use of such flexible thread-type, tape-type or membrane-type structures as the connection piece between the joint parts that move opposite one another is thus of great advantage. Such a connection piece makes possible a certain flexibility of the joint. Connecting threads or woven fabric parts can flex and even twist in all directions, without the danger thereby of an increased material wear or fatigue. A play space between the joint parts and therefore in the freedom of movement of the joint can be guaranteed without limitation. Also, an intense stressing of the joint by very frequent flexing and extending will hardly lead to material fatigue.

In joints, which should be held together by the connection piece over a lifetime, the thread-type or woven-fabric-type connection piece is comprised advantageously of a material that cannot be resorbed by the body.

Appropriately, there is a lateral play space between groove and connection piece, so that the connection piece is not sheared off at the joint part with a lateral movement, and does not scrape on the surface of the groove.

Appropriately, joint parts can be joined next to one another by several thread-type and/or woven-fabric-type connection pieces. In this way, a lateral deflexion of the joint is limited and the lever ratio between joint part and connection piece is favorably influenced.

Advantageously, an elevation is present in the concave joint part that works together with a depression e.g., a channel, furrow or groove in the convex joint part, and the lateral freedom of movement of the joint is limited by the assured play space between depression and elevation. In this way, abrasion-resistant materials are present at the contact points of the two condyles. Also, limitation of the freedom of movement can be designed by the shapes of the elevation and depression. The play space of movement relative to flexion in the principal flexion direction (flexion) and deflection crosswise to this (lateroflexion) can be very precisely defined by a depression in one condyle and an elevation, which cooperates with it, in the other condyle. This play space is also important for the permanence of the anchoring of the prosthesis in the bone. It reduces the transfer of shearing and transverse forces onto the anchoring of the prosthesis. These forces must thus, as a rule, be taken up by the tendons and the capsule tissue.

The surface of the elevation or the depression and the transition parts bounded thereby and the adjacent sliding surfaces or the actual joint surfaces are together characterized as the contact surface. The depression can coincide with the groove, but it can also be formed independent of it.

Advantageously, the lateral freedom of movement and/or the freedom of movement in the flexion direction of the joint is limited by the assured play space between sliding surfaces adjacent to the groove and sliding surfaces of the concave joint part interacting with the first surfaces. The freedom of movement can vary each time depending on the shape of the contact surfaces and depending on the length and attachment point of the connection piece, or according to the position of the point of rotation of the joint relative to the body axis of the convex joint part. Thus, the natural kinematics of the human joint will be reproduced. For the proximal (PIP) and distal (DIP) interphalangeal joints (IP joints) and toe joints, the sliding surfaces of the joint parts are advantageously at least partially cylindrical or truncated-cone-shaped, in order to prevent a lateral deflection of the members coupled by the joint. Preferably, there is such a sliding surface both for the convex condyle as well as for the concave condyle, comprised of two oppositely inclined truncated-cone surfaces with the same cone axis. In this way, a lateral displacement of the joint parts relative to one another can also be prevented.

Expressed in general terms, it can be stated that at least one part of the sliding surfaces with respect to their cross section, and appropriately on both sides of the connection piece, is formed in such a way that the places at which lines on one side of the connection piece that are perpendicular to the surface of these parts of the sliding surfaces approach or intersect the body axis, are set at a distance from the corresponding places of the corresponding lines on the other side of the connection piece. And in fact, these places may lie on the side of the connection piece, on which the corresponding sliding surface also lies, or, however, they may lie on the other side. Accordingly, the sliding surfaces run together toward the groove, such that they would form together a ridge or even a channel or a furrow in the absence of the groove. In this way, movement is limited by exercising pressure on the sliding surfaces and pulling on the connection piece.

For an angle of 90° between the movement direction and contact surface, the limitation of movement is clear, and for small angles, the limit can be widened by stretching the connection piece. The limit of the freedom of movement is thus weaker, the smaller this angle.

Advantageously, an axis is present in the convex joint part, around which a loop of the connection piece is guided. In this way, the connection piece will not be flexed during flexion and extension of the joint, but it will slide, as a rule without load, around the axis, which has almost no effect on the aging of the connection piece, relative to wear and fatigue. A single axis can be present, or an axis can be present in both joint parts. The axes may be arranged rigidly or can be rotated in the joint part.

Advantageously, at least one of the joint parts is inserted by translation movement in a sheath attached in the bone. This sheath prevents the tensile forces, which occur very appropriately in the hand, from being transmitted to the anchoring of the joint part. Tensile forces must thus be taken up by the tendons and the tissue of the capsule. This has the advantage that the endoprosthesis cannot be torn from its anchoring. Such sheaths can also be designed such that a rotation of the prosthesis around the axis of the finger or toe will not be transmitted to the joint, but rather the joint part rotates in the sheath. The mounting of the sheaths is very simple as another advantage, and is conducted by screwing the sheath into the bone marrow channel.

Appropriately, the elevation is longer or shorter in the flexion direction, depending each time on the rotation play space to be guaranteed. A longer elevation permits a smaller rotation with the same play space.

Advantageously, the groove is broader or narrower, each time depending on the flexion angle, so that the lateral play space is different, depending on the position of the joint. In this way, possible lateroflexion can be controlled as a function of flexion.

The elevation advantageously surrounds the connection piece and thus the connection piece cannot rub against the contact surface of the condyle, particularly the depression.

Advantageously, the curve at the concave condyle, which curve is formed by the elevation and the adjacent sliding surface, in a cross section crosswise to the bending direction on one side of the joint, corresponds to the curve at the convex condyle, which is formed by the depression and the adjacent sliding surface. In this way, the contact surfaces lie at least linearly, and preferably flatly, against one another under load, so that high point loads and thus the increased abrasion that results are avoided.

Advantageously, the body axis of the convex joint part and the axis of rotation around which the concave joint can be pivoted, are distanced from one another. In this way, the play space between the sliding surfaces is different each time, depending on the flexion position. In this way, the lateral freedom of movement is also different, each time depending on the flexion position.

Advantageously, the sliding surfaces are spherical surfaces, the spherical centers of which are distanced relative to one another. In this way, a planar contacting of the sliding surfaces is practically given in any load case. For flexion without play space between the sliding surfaces, both spherical sliding surfaces of the concave condyle lie flat against the corresponding sliding surfaces of the convex condyle and move around the axis via the two spherical centers. In the case of lateroflexion and simultaneous flexion of the joint, one or the other sliding surfaces is flatly applied, depending each time on the direction of the lateral deflection, while the other sliding surface is removed.

BRIEF DESCRIPTION OF THE FIGURES

Here:

FIG. 3 shows an example of embodiment with a cord-type connection piece guided around an axis on one side a) in longitudinal section and b) in bottom view;

FIG. 4 shows an endoprosthesis with pin and groove and/or elevation and depression, cut away on the left, and in view on the right;

Figure 7A:
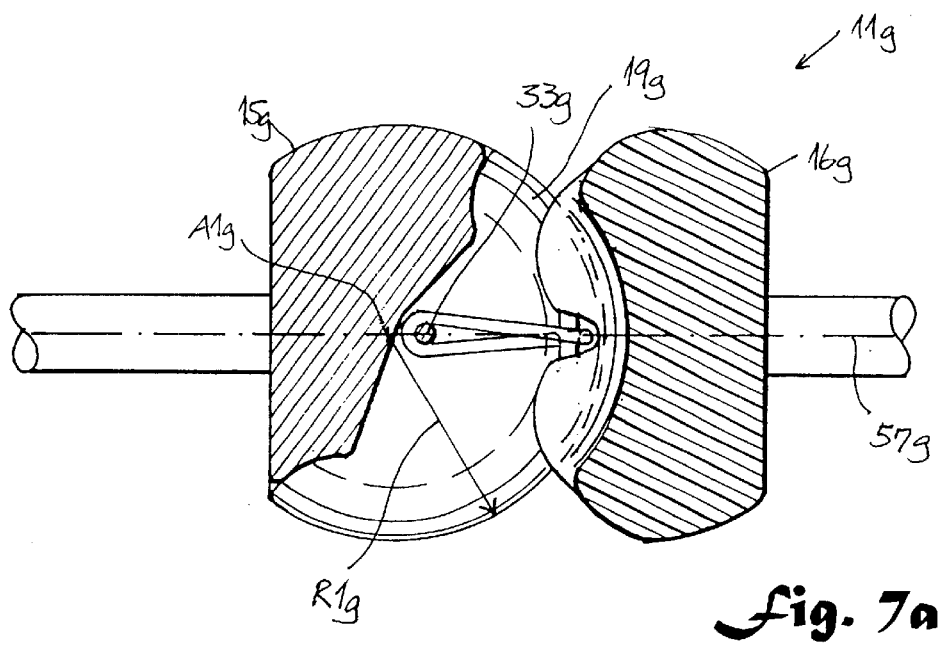
Figure 7B:
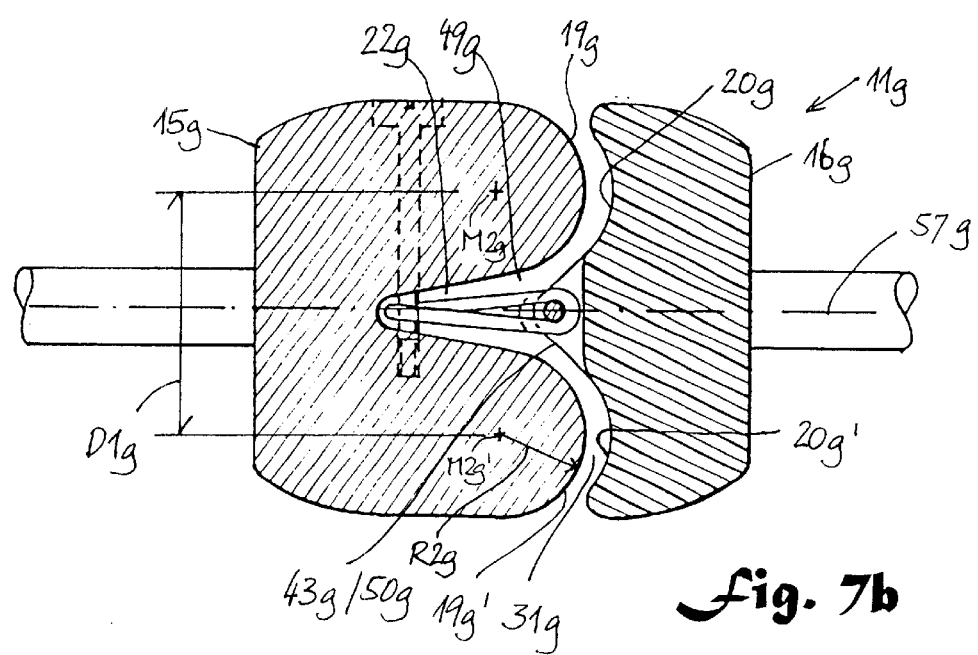
Figure 8A:
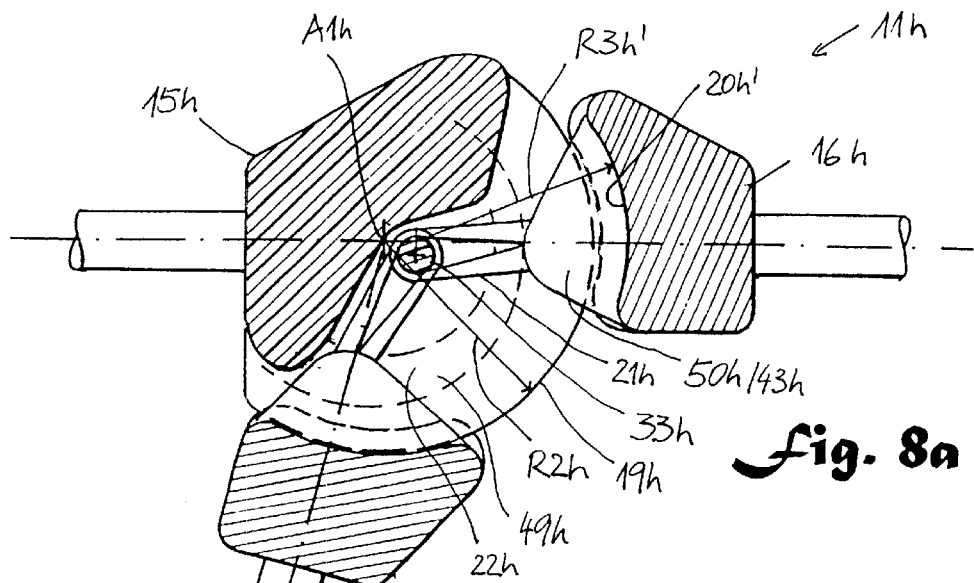
Figure 8B:
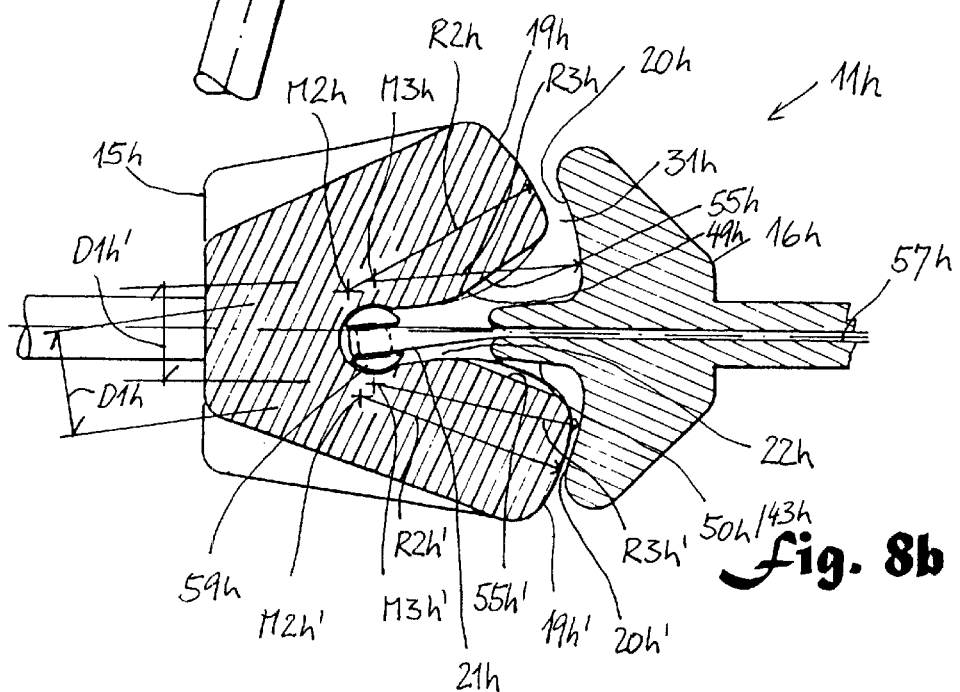
Figure 9A:
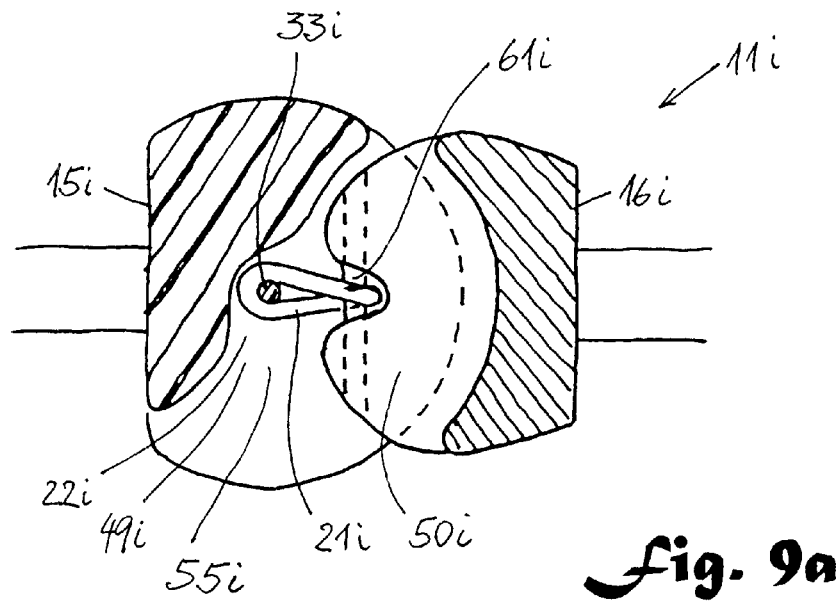
Figure 9B:
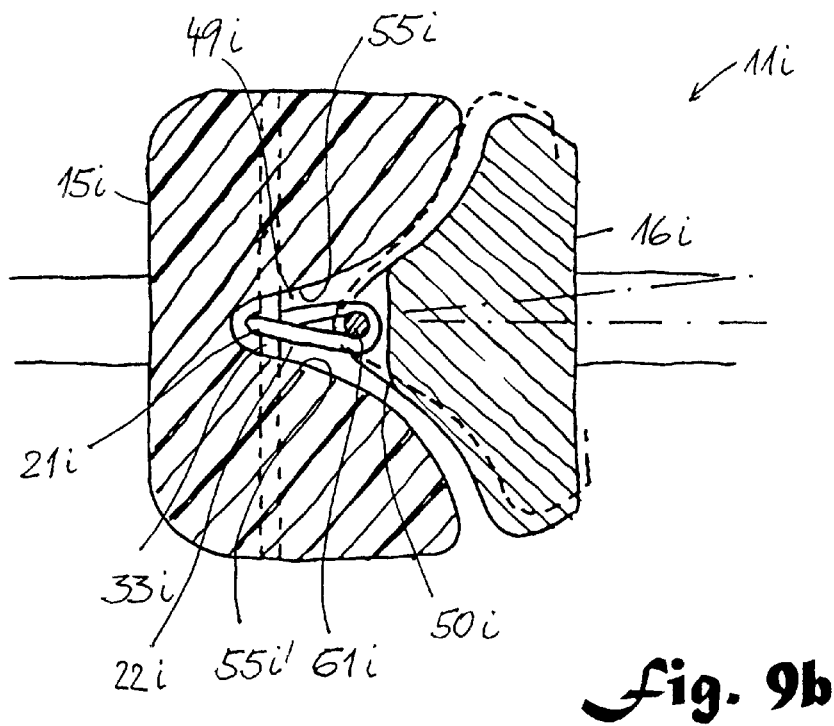

a) in vertical section, b) in horizontal section and c) the spherical condyle in frontal view;

FIG. 7 shows a finger joint endoprosthesis with two ring-shaped sliding surfaces on both sides of a depression, a) in vertical section, b) in cross section;

FIG. 8 shows an MCP joint endoprosthesis with two spherical sliding surfaces on both sides of the depression and of the elevation, a) in vertical section, b) in cross section;

FIG. 9 shows a finger joint prosthesis with two spherical contact surfaces, whereby each of the sliding surfaces and the adjacent contact surface of the elevation or of the depression are together spherical;

a) in vertical section, b) in cross section; and

Figure 10:
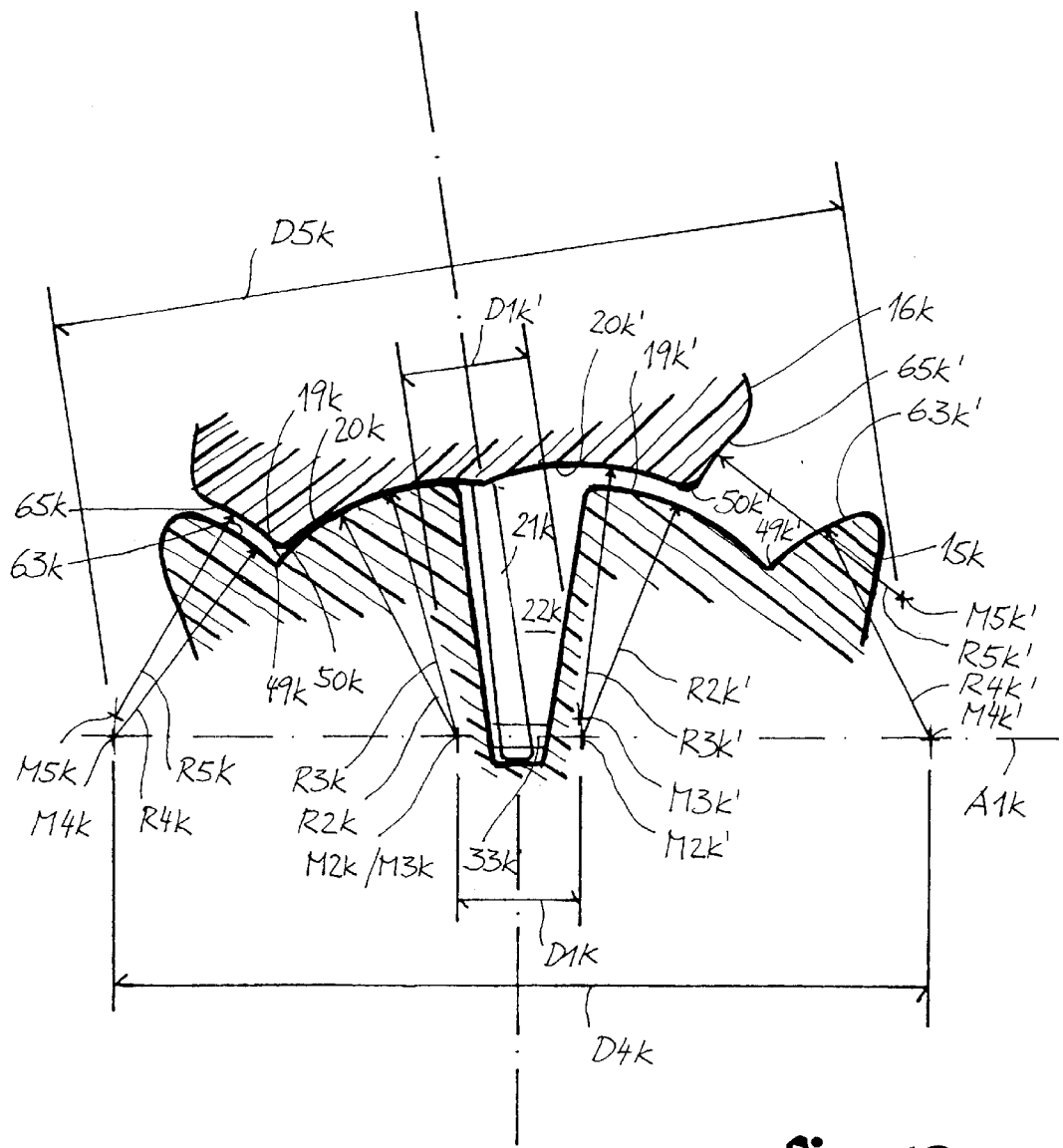

FIG. 10 shows a schematic representation of a joint geometry with a contact surface with four spherical centers.

DESCRIPTION OF EXAMPLES OF EMBODIMENT

Figure 1A:
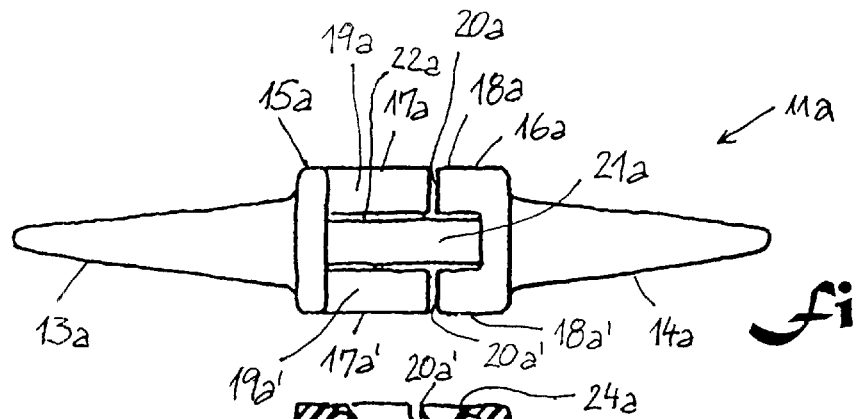
FIG. 1 shows an example of embodiment that can be produced in one piece with a tape-type connection piece, a) in a bottom view and b) in vertical section.
Figure 1B:
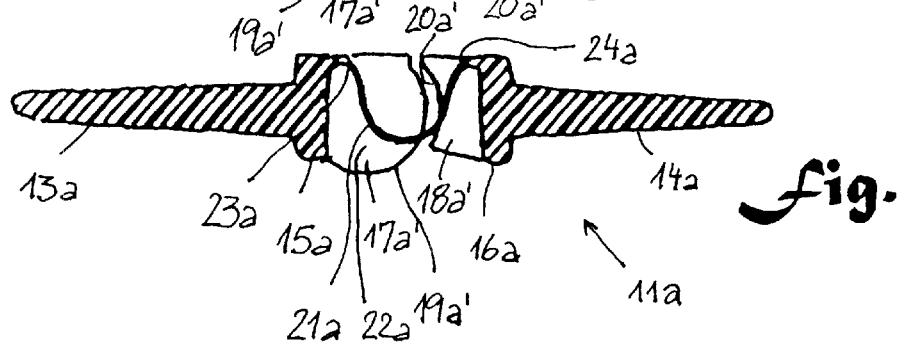

A very elementary example of embodiment of an endoprosthesis according to the invention is designated by $11a$ in FIG. 1. It is produced in one piece and has two pins $13a$ and $14a$ at two condyles $15a$ and $16a$. Condyles $15a$, $16a$ laterally have two head pieces $17a$, $17a'$ and $18a$, $18a'$, which form approximately equal and oppositely shaped sliding surfaces $19a$, $19a'$ or $20a$, $20a'$, respectively. A tape-type connection piece $21a$ is arranged in a central region between two such pairs of sliding surfaces. This connection piece $21a$ describes a curve arched between the two condyles $15a$ and $16a$. It is separated laterally by head pieces $17a$, $17a'$, $18a$, $18a'$ and its beginning $23a$ and its end $24a$ are connected to a condyle $15a$, $16a$, each time. The transition from tape-type connection piece $21a$ to condyle $15a$, $16a$ runs into the thickness. The tape-shaped connection piece $21a$ is now deformed upon flexion of the joint over its entire length. Thanks to its thin cross section and the deformable length of the connection piece, there is only a slight danger of a fatigue break.

For lateral deflection, pressure is exercised on two sliding surfaces (e.g. $19a$ and $20a$), while connection piece $21a$ comes under tensile load. Due to the fact that connection piece $21a$ is guided in groove $22a$ between the two head pieces $17a$, $17a'$, a lateral displacement of the two joint parts $15a$ and $16a$ is also prevented.

An example of embodiment $11b$ is shown in FIGS. $2a$ and $b$, in which connection piece $21b$ is a thread or a cord. The thread or the cord is anchored in both joint parts $15b$, $16b$. When the joint moves, connection piece $21b$ is bent. By selecting the site $25b$, at which cord $21b$ exits from attachment opening $27b$ in joint part $15b$, the play space between joint parts $15b$, $16b$ can be selected to remain constant, or can be selected as different, depending on the position of joint parts $15b$, $16b$, relative to one another. The thread or cord $21b$ runs in convex condyle $15b$ in a slot $22b$. The slot or groove $22b$ limits the lateral movement play space of joint $11b$, acting together with cord $21b$. Due to the flexibility of cord $21b$ in all directions and play space $31b$ between sliding surfaces $19b/b'$ and $20b$, there is a certain movement play space also crosswise to the flexion direction of the joint. Since cord $21b$ only takes up tensile forces, usually the joint cavity or the concave condyle $16b$ slides on the convex condyle $15b$, without the presence of a connection piece $21b$ between the two parts $15b$, $16b$ being detectable. However, a dislocation of joint $11b$ and physiologically inappropriate movements are effectively counteracted by connection piece $21b$. In the case of a lateroflexion of the joint, the outer regions of condyles $15b$, $16b$ line up next to one another and cord $21b$ is tensed. In the case of a negative flexion out beyond the extension position, thus a movement of joint part $16b$ upward in FIG. $2a$, or in the counter-clockwise direction, contact surfaces $19b$, $19b'$ and $20b$ of the two joint parts are guided opposite one another. The movement curve of joint part $16b$ intersects the curve of contact surface $19b/b'$ of joint part $15b$, since the point of rotation for the rotation of joint part $16b$ in this direction lies close to the surface $19b$ of convex condyle 17.

FIG. 3 shows an example of embodiment $11c$ of an endoprosthesis with a convex condyle $15c$ and a concave condyle 16c. An axis of rotation 33c is arranged approximately on the body axis of the roughly cylindrical condyle 15c, and two threads or cords 21c run around this axis of rotation. These cords 21c form the connection piece. The connection piece 21c runs in a slot 22c between the two head pieces 17c and 17c'. Instead of two threads or cords 21c, a tape could also be used: either a single cord or thread or two or more threads or cords could also be used. A play space 31c, which gives joint parts 15c and 16c the possibility of slightly twisting relative to one another and to be laterally deflected or bent at a sharp angle is provided between convex condyle 15c and concave condyle 16c. A stop 35c, which limits the freedom of movement upward in cooperation with the upper edge 37c of concave condyle 16c, is arranged on the upper side of condyle 15c. Due to the fact that connection piece 21c is manufactured of a flexible material, a large play space 31c can be left relative to the joint, without the danger that connection piece 21c scrapes against axis of rotation 33c, that it buckles, or that the joint is dislocated. Material wear and deformations of the prosthesis are also prevented as well as too precise a guiding and the dislocation of the joint. The movement play space is defined by play space 31c and the shape of condyles 15c, 16c.

Connection piece 21c is fastened in endoprosthesis 11c in pin 14c. The two ends of cord 21c were introduced into opening 39c of tube-shaped pin 14c and rigidly clamped, welded or glued therein. In concave head part 16c, outlet opening 41c is opened up into a funnel shape, and thus cord 21c cannot rub against a sharp edge. In contrast to the joint represented in FIG. 2, the prosthesis shown in FIG. 3 has the advantage that connection piece 21c is not bent during flexion of the joint.

The example of embodiment 11d illustrated in FIG. 4 is formed in a similar manner. Instead of a stop (FIG. 3a; 35c) a pin 43d running in slot 22d limits the movement play space of prosthesis 11d by cooperating with the edge 45d of slot 22d. Pin 43d surrounds cord 21d and also has a lateral play space. It protects the flexible connection piece 21d against rubbing at edge 47d of slot 22d in convex condyle 15d and limits lateral displacement and lateroflexion. Pin 43d is part of concave joint cavity 16d.

Figure 5:
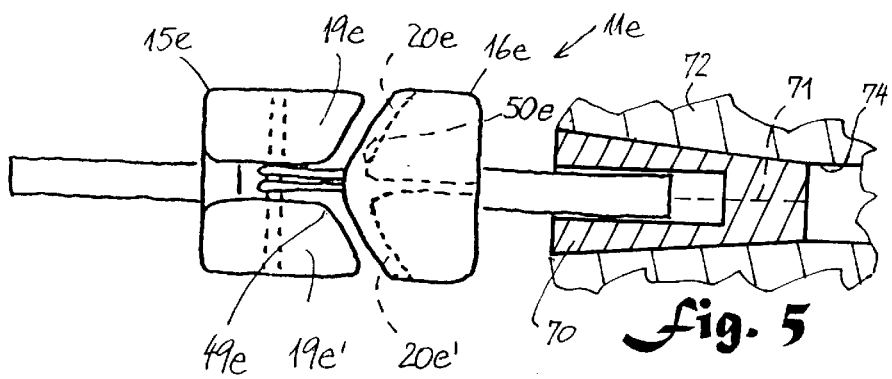
FIG. 5 shows an endoprosthesis with conical sliding surfaces.

Another possibility for preventing possible lateral displacement and for limiting lateroflexion as well as rotation of a joint is presented in FIG. 5. The sliding or contact surfaces 19e, 19e' and 20e, 20e' are shaped as truncated cone surfaces and are complementary. One could also say that convex condyle 15e has a central depression 49e and the concave condyle has a central elevation 50e of contact surfaces 19e/e' or 20e/e'. As a result of the inclination of the sliding or contact surfaces, condyles 15e and 16e must move apart and thus a lateral displacement of condyles 15e, 16e can occur relative to one another. This moving apart is prevented by connection piece 21e.

Figure 2A:
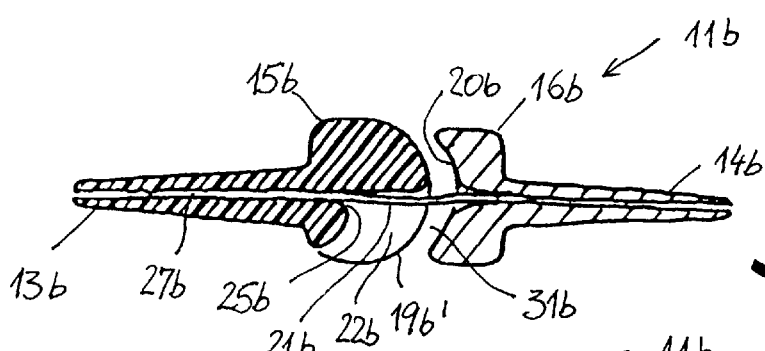
FIG. 2 shows an example of embodiment with a cord-shaped or thread-shaped connection piece solidly anchored on both sides a) in longitudinal section and b) in bottom view.
Figure 2B:
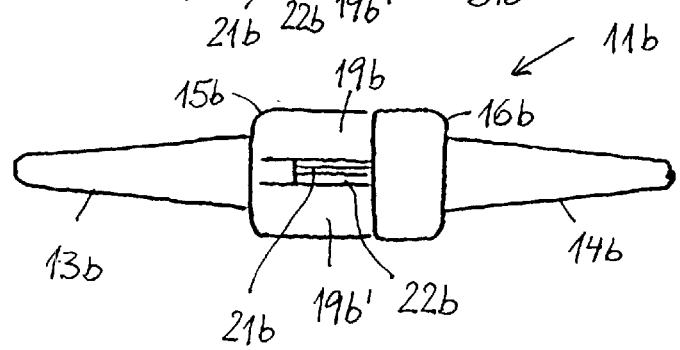
Figure 6A:
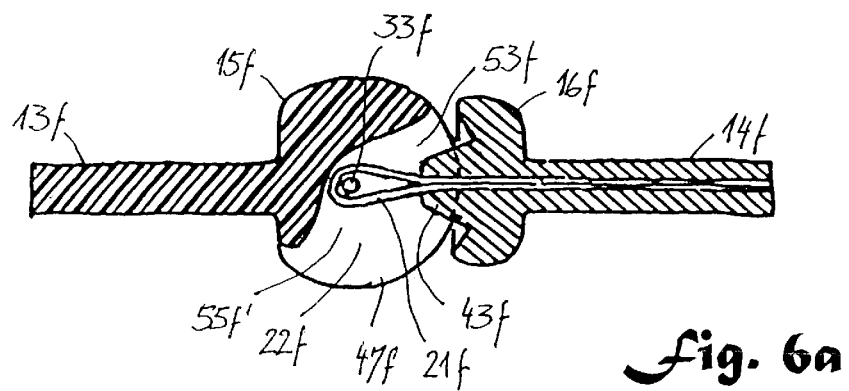
FIG. 6 shows an endoprosthesis for the MCP joint with spherical condyle, pin and enlarged lateral play space in the extended position.
Figure 6B:
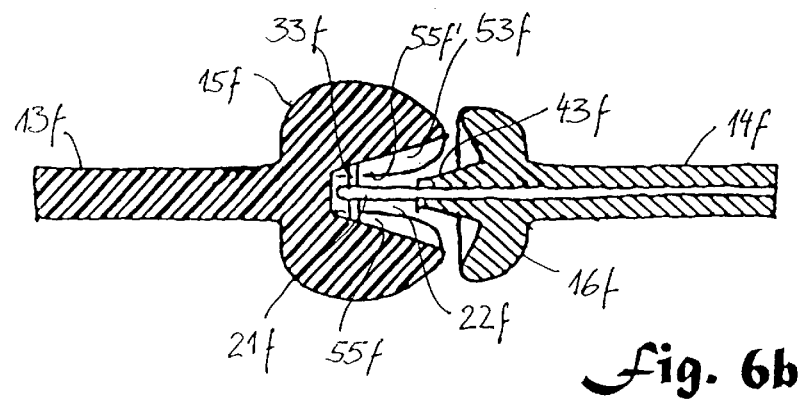
Figure 6C:
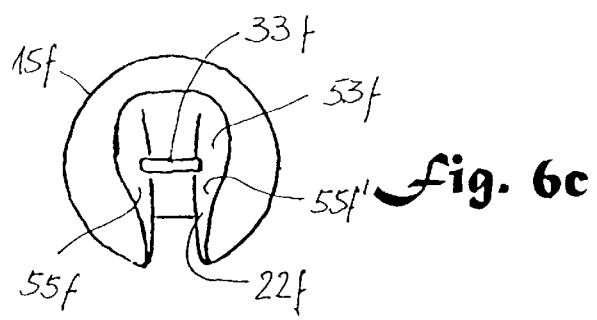

A joint 11f, which is designed for the MCP joint and is similar to the joint in FIGS. 2 to 4 is shown in FIG. 6. Due to its essentially spherical shape, the convex condyle 15f permits the counterpiece 16f equipped with a concave cavity to be deflected on all sides. Since the natural MCP joint permits a greater lateral deflection in the extended position than in the flexed position, the endoprosthesis is designed in the same way for this joint. A pin 43f limits the movement play space thereto, cooperating with edge 47f of slot 22f. The slot or groove 22f now partially has an expansion 55f (see FIG. 6c), so that pin 43f receives more space for a lateral movement in an extended position of the joint. In contrast, in the flexed position, less intermediate space is found between pin 43f and lateral surfaces 55f, 55f, so that joint 11f can be moved essentially only in one direction, as in the case of the natural joint.

An MCP joint prosthesis 11g is shown in FIG. 7, in which, contact surfaces 19g, 19g', or 20g, 20g' on both sides of slot 22g or depression 49g, or of pin 43g or elevation 50g, have a surface shape, which describe in the flexion direction an orbit with a maximal radius R1g around axis A1g and crosswise to this, an orbit with smaller radius R2g. This shape assures that practically any load of the contact surfaces leads to the fact that these contact surfaces lie at least linearly relative to one another, despite the play space 31g between condyles 15g and 16g.

Now the lateral deflectability, the possible rotation and the play space 31g of joint 11g can be defined relative to one another by play space 31g and radii R2g, R2g' as well as distance D1g from circular centers M2g and M2g'. As is shown in the example, if flexion axis A2g of the joint does not lie on axis A1g of contact surfaces 19g, 19g', 20g, 20g', play space 31g and, because of this, the maximal possible lateroflexion and rotation, is also dependent on the flexion position.

Contact surfaces 20g, 20g' of concave condyle 16g do not form the precise counter-shape of contact surfaces 19g, 19g' of convex condyle 15g, since, if they did, a lateral deflection would not be possible. The sliding surfaces 20g, 20g' are circular in the cross-sectional line through axis 57g of the finger. The further the cross section is removed from this axis 57g, the greater the cross-sectional line is expanded outwardly, which flattens the curve. The sliding surfaces 19g' and 20g, or 19g' and 20g' lie next to one another under any angle of deflection on a circle around axis A1g.

Thus, if the sliding surfaces are to be applied flatly against each other at any angle of lateroflexion, they must be spherical. A joint prosthesis 11h for the MCP joint of the left index finger is shown in FIG. 8, which prosthesis has two spherical sliding surfaces 19h, 19h', 20h, 20h' per joint part. The sliding surfaces 19h and 19h' each have a spherical center M2h, M2h'. The spherical centers M2h, M2h' are separated from each other by a distance D1h. The two concave spherical surfaces of sliding surfaces 20h, 20h' have the same diameter. Their central points M3h, M3h' are arranged at a distance D1h' from each other, whereby the lengths of distances D1h and D1h' and the radii R2h and R3h as well as R2h' and R3h' of the sliding surfaces correspond. It may be of advantage if radii R2h and R3h are smaller or larger with respect to radii R2h' and R3h'. In practice, the radii of concave sliding surfaces 20h, 20h' will be somewhat larger than the radii of convex sliding surfaces 19h, 19h', since a liquid film will be found in the implanted joint 11h between sliding surfaces 19h/19h', on the one hand, and 20h/20h', on the other hand.

Axis 33h for connection loop 21h lies approximately next to axis A1h through central points M2h and M2h', so that the play space 31h between the sliding surfaces is smaller or larger, each time depending on the angle of flexion. The maximal play space 31h is approximately 15° in the example for a flexion position. Play space 31h is approximately 100° to zero, so that the joint cannot be further flexed.

The possible lateral deflection is smaller or larger, corresponding to the play space 31h that is present. If the sliding surfaces are contacted at 100° of flexion, the possible lateroflexion is almost zero, and is approximately 45° for an extended finger or a finger bent slightly to 15°.

Axis A1h runs through central points M2h and M2h' at an angle of approximately 97.5° crosswise to the extended finger axis 57h. In this way, the finger can be deflected by 15° more from the extended state on the side of sliding surfaces 19h, 20h than on the side of sliding surfaces 19h', 20h'. When the joint is loaded, whereby the finger is pressed against the metacarpus, pressure is thus first exercised on sliding surfaces 19h', 20h'. In this way, the finger is deflected to the center of the hand. Also, a flexion can incline the finger to the center of the hand. The natural joint axes are optimally respected by this joint construction.

Axis 33h is formed by a unit 59h with spherical contact surfaces relative to a spherical hollow space and can be engaged in this hollow space and can be rotated therein. In this way, axis 33h can be twisted in all directions. Loop 21h is guided flatly around axis 33h and anchored in concave joint part 16h, particularly in its stem or shaft 14h. The loop takes up changes in the position of axis 33h relative to finger axis 15h, in that it is deformed. When the finger is extended, loop 21h is loose; only with strong lateroflexion or flexion does it prevent a further movement of joint parts 15h, 16h toward one another and thus also a luxation.

Elevation 50h is formed corresponding to sides 55h/55h' of depression 49h, so that if concave joint part 16h is deflected up to the stop of elevation 50h at side 55h, the latter contact one another in a flat manner.

For joints with smaller lateroflexion, such as the proximal or distal interphalangeal joints (PIP, DIP), a flat contact, a large play space between the joint parts and a small lateroflexion are achieved, if the spherical central points are moved as far apart as possible, as shown in FIG. 9. If the distance from the spherical central points is greater than the sum of the two spherical radii, a depression is formed, whose sides, 55i, 55i' lie on the spherical surface. In addition, two axes 33i and 61i for the connection loop 21i are shown in FIG. 9. Loop 21i is ring-shaped. It is guided in convex joint part 15i and in concave part 16i around two axes 33i arranged perpendicular to one another.

The joints can also be configured in other ways within the scope of the invention, and they may have three or even four or more sliding surfaces, preferably spherical. In this way, the contact surfaces between the two joint parts can be kept large during a lateroflexion and for the laterally extended position. This is of interest, for example, in the case of a hand joint.

Such a hand joint prosthesis 11k is shown schematically in cross section in FIG. 10. Again, radii R2k, R2k', R4k, R4k' of sliding surfaces 19k, 19k', 63k, 63k' of the convex joint part 15k correspond to the radii R3k, R3k', R5k, R5k' of sliding surfaces 20k, 20k', 65k, 65k' of concave joint part 16k. Distances D1k and D1k' between central points M2k and M2k' or M3k and M3k' are equally large. The distance D4k between M4k and M4k', however, is larger than the distance D5k between M5k and M5k'. In the case of a lateroflexion, joint part 16k is moved each time around central point M3k or M3k' until sliding surfaces 63k and 65k or 63k' and 65k' line up next to one another. The spherical central points of all sliding surfaces for the case of the convex joint part 15k lie on an axis A1k, and in the case of the concave joint part, on two axes intersecting at the center of the joint. In this way, the flexion of the joint is always conducted around the same axis A1k through central points M4k, M2k, M2k', M4k'. However, the concave joint part 16k can be tilted laterally.

The closer the central points, e.g., M2k and M4k, which lie on one side, are to each other, the weaker is the limit of the lateral freedom of movement. With a suitable play space, a sliding over several spherical surfaces next to one another is hardly possible, whereby only a maximum of two adjacent spherical surfaces come in contact with the corresponding surfaces of the concave joint part.

Such geometries of the joint parts are basically conceivable even without the connection piece and without the groove provided for this. It is also conceivable that one of the joint parts is comprised of two parts, which are joined in all cases by means of a cord-type connecting piece, e.g., for a hand joint. The parts can be slightly inclined relative to one another. One of these could be attached to the ulna and the other to the radius.

In summary, it can be stated that for an endoprosthesis (11) for a joint, the two interacting joint parts (15, 16) are joined by a cord-type connection piece (21), which is attached in the vicinity of the body axis (A1, e.g., M2h, M2h') of the convex condyle (15) and stretched through a lengthwise groove (22) in the flexion direction of the joint. The connection piece assures a play space (31) between the contact surfaces (19, 20) of joint (11). It is protected from friction on groove wall (55) by an elevation (50, 43) in concave joint part (16). An elevation (43, 50) at concave joint part (16) and a depression (49) at convex joint part (15) interact in such a way that the lateral movement play space between depression and elevation determines the freedom of movement with respect to lateroflexion of the joint. In advantageous forms of embodiment, at least one pair of corresponding sliding surfaces (e.g. 19, 20 . . . ) are applied flatly on one another on the two condyles, thanks to the spherical surfaces, when a load occurs in any position of the joint.

Reference List a, b . . . examples of embodiment
a, a' corresponding parts on either side of the connection piece for the same condyle
11 endoprosthesis
13 stem at the convex condyle for implanting in the bone marrow channel
14 stem at the concave condyle for implanting in the bone marrow channel
15 convex condyle
16 concave condyle
17 head part on one side
18 head part on the other side
19 sliding surfaces at the convex condyle
20 sliding surfaces at the concave condyle
21 connection piece, e.g. cord, tape . . .
22 depression, e.g. slot, groove
23 beginning of the connection piece
24 end of the connection piece
25 outlet place of the connection piece from the fastening channel
27 fastening channel
31 play space between the sliding surfaces
33 axis of rotation for the connection piece
35 stop
37 edge at the concave joint part
39 fastening opening
41 rounded outlet opening
43 elevation
45 edge of the depression 22, 49, forming an articulation stop for elevation 43, 50
47 edge of the side wall 55
49 depression, e.g. furrow, channel
50 elevation, e.g. ridge
53 broadening of the depression
55 side wall 57 axis of the finger
59 engagable unit with axis for connection piece
61 axis for connection piece at the concave condyle
63 additional sliding surfaces at the convex condyle
65 additional sliding surfaces at the concave condyle
A1 body axis of the convex condyle
M2 central point for the arc of the convex sliding surfaces
M3 central point for the arc of the concave sliding surfaces
M4 central point for another convex sliding surface
M5 central point for another concave sliding surface
R2 radius of a sliding surface proceeding from M2
R3 radius of a sliding surface proceeding from M3
R4 radius of a sliding surface proceeding from M4
R5 radius of a sliding surface proceeding from M5

What is claimed is:

1. Endoprosthesis for a joint, with a proximal and a distal joint part, of which one joint part in the flexion direction has an essentially convex contact surface around a body axis, and the other has a corresponding essentially concave contact surface, whereby the joint parts are joined with a flexible connection piece taking up tensile forces and which connection piece comprises at least one element selected from the group consisting of thread elements and tape elements, characterized in that:

the connection piece defines a play space between said essentially convex contact surface and said essentially concave contact surface;

a depression is formed in said one joint part longitudinally extending in a flexion direction; and the connection piece is fastened in the depression or at a base of the depression, whereby a lateral play space is formed between the depression and the connection piece and wherein said depression accommodates flexion movement more than lateral movement.

2. Endoprosthesis according to claim 1, further characterized in that the lateral play space is effective to limit lateral freedom of movement.

3. Endoprosthesis according to claim 1, further characterized in that the width of the depression adjacent the connection piece varies depending on the angle of flexion, so that the lateral freedom of movement is different depending on the joint position.

4. Endoprosthesis according to claim 1, further characterized in that:

the connection piece runs around an axle in said one joint part which defines a flexion axis of rotation of said other joint part about said one joint part; and an axis of curvature of the convex contact surface and the flexion axis of rotation are distanced from one another.

5. Endoprosthesis according to claim 1, further characterized in that said convex contact surface, when viewed in section through said convex contact surface and including a flexion axis of rotation of said other joint part about said one joint part, has first and second surface portions on either side of said depression and wherein, when so viewed, lines normal to said first and second surface portions respectively approach said flexion axis of rotation at first and second sides of a central plane normal to said flexion axis of rotation.

6. Endoprosthesis according to claim 5, further characterized in that, when so viewed, the first and second surface portions have respective first and second centers of curvature separated from each other.

7. Endoprosthesis according to claim 1, characterized in that at least one of the joint parts is insertable by a translation movement into a sheath attachable in a bone so as to prevent tensile forces from being transmitted to said sheath.

8. Endoprosthesis according to claim 7, characterized in that the sheath is attachable by screwing it into a marrow channel of the bone.

9. Endoprosthesis according to claim 7, characterized in that the joint part insertable in the sheath is rotatable around a sheath axis.

10. Endoprosthesis for a joint, with a proximal and a distal joint part, of which one joint part in the flexion direction has an essentially convex contact surface around a body axis, and the other has a corresponding essentially concave contact surface, whereby the joint parts are joined with a flexible connection piece taking up tensile forces and which connection piece comprises at least one element selected from the group consisting of thread elements and tape elements, characterized in that:

the connection piece defines a play space between said essentially convex contact surface and said essentially concave contact surface;

a depression is formed in said one joint part longitudinally extending in a flexion direction;

the connection piece is fastened in the depression or at a base of the depression, whereby a lateral play space is formed between the depression and the connection piece; and an elevation on said other joint part cooperates with the depression to limit at least relative lateral freedom of movement of the proximal and a distal joint parts.

11. Endoprosthesis according to claim 10, characterized in that the elevation surrounds a part of the connection piece.

12. Endoprosthesis according to claim 10, characterized in that when viewed in section through the convex contact surface and including a flexion axis of rotation of said other joint part about said one joint part, surface curvature of the elevation and of an adjacent portion of the adjacent concave contact surface is complementary to surface curvature an adjacent portion of the convex contact surface.

13. Endoprosthesis for a joint, with a proximal and a distal joint part, of which one joint part in the flexion direction has an essentially convex contact surface around a body axis, and the other has a corresponding essentially concave contact surface, whereby the joint parts are joined with a flexible connection piece taking up tensile forces and which connection piece comprises at least one element selected from the group consisting of thread elements and tape elements, characterized in that:

a depression is formed in said one joint part longitudinally extending in a flexion direction;

an axle is attached to said one joint part and extends across the depression;

the connection piece has an end connected to said other joint part; and the connection piece includes a loop portion around the axle whereby a lateral play space is formed between the depression and the connection piece and the connection piece defines a play space between said essentially convex contact surface and said essentially concave contact surface.

14. Endoprosthesis for a joint, with a proximal and a distal joint part, of which one joint part in the flexion direction has an essentially convex contact surface around a body axis, and the other has a corresponding essentially concave contact surface, whereby the joint parts are joined with a flexible connection piece taking up tensile forces and which connection piece comprises at least one element selected from the group consisting of thread elements and tape elements, characterized in that:

the connection piece defines a play space between said essentially convex contact surface and said essentially concave contact surface;

a depression is formed in said one joint part longitudinally extending in a flexion direction;

the connection piece is fastened in the depression or at a base of the depression, whereby a lateral play space is formed between the depression and the connection piece; and an axle is arranged in the depression, and the connection piece includes a loop portion around the axle and wherein the play space and lateral play space are effective to limit lateral freedom of movement.

15. Endoprosthesis for a joint, with a proximal and a distal joint part, of which one joint part in the flexion direction has an essentially convex contact surface around a body axis, and the other has a corresponding essentially concave contact surface, whereby the joint parts are joined with a flexible connection piece taking up tensile forces and which connection piece comprises at least one element selected from the group consisting of thread elements and tape elements, characterized in that:

a depression is formed in said one joint part longitudinally extending in a flexion direction;

an axle is attached to said one joint part and extends across the depression;

the connection piece has an end connected to said other joint part;

the connection piece includes a loop portion around the axle, whereby a lateral play space is formed between the depression and the connection piece;

the connection piece defines a play space between said essentially convex contact surface and said essentially concave contact surface; and an elevation on said other joint part cooperates with the depression to limit at least relative lateral freedom of movement of the proximal and a distal joint parts.

16. Endoprosthesis for a joint selected from the group consisting of finger, toe and hand joints, with a proximal and a distal joint part, of which one joint part has an essentially convex contact surface, and the other has a corresponding essentially concave contact surface, wherein:

the joint parts are joined with a flexible connection piece selected from the group consisting of thread and tape elements, taking up tensile forces between the joint parts and connecting the joint parts to permit sliding flexion movement of the joint parts from an extended position to a flexed position;

a depression is formed in the convex joint part and longitudinally extends in a flexion direction, said connection piece extending through the depression; and the depression has a width defining a lateral play space between the depression and the connection piece, permitting movement of the connection piece within the depression during flexion movement and lateral movement of the proximal and distal joint parts and wherein said depression accommodates said flexion movement more than said lateral movement.

17. Endoprosthesis according to claim 16, wherein the connection piece has a length effective to provide a play space between the contact surfaces.

18. Endoprosthesis according to claim 16, wherein the depression width decreases in the flexion direction to provide a decreasing lateral play during the flexion movement.

* * * * *